(12) United States Patent
Kenyon et al.

(10) Patent No.: US 6,397,841 B1
(45) Date of Patent: Jun. 4, 2002

(54) APPARATUS FOR SUPPLYING BREATHABLE GAS

(75) Inventors: Barton John Kenyon, Worcester (GB); Dion Charles Chewe Martin, Concord (AU)

(73) Assignee: ResMed Limited, North Ryde (AU)

( * ) Notice: Subject to any disclaimer, the term of this patent is extended or adjusted under 35 U.S.C. 154(b) by 0 days.

(21) Appl. No.: 09/099,665

(22) Filed: Jun. 18, 1998

(30) Foreign Application Priority Data

Jun. 18, 1997 (AU) .............................................. PO7422

(51) Int. Cl.[7] .............................................. A62B 18/00
(52) U.S. Cl. .............................. 128/202.27; 128/204.14; 128/204.18
(58) Field of Search ....................... 128/202.27, 204.14, 128/204.18, 203.12, 203.18, 203.16, 203.14, 204.13, 204.15

(56) References Cited

U.S. PATENT DOCUMENTS

| | | |
|---|---|---|
| 2,712,927 A | 7/1955 | Blum |
| 2,904,033 A | 9/1959 | Shane |
| 2,953,355 A | 9/1960 | Hungate |
| 3,099,985 A | 8/1963 | Wilson et al. |
| 3,502,100 A | 3/1970 | Jonson |
| 3,559,638 A | 2/1971 | Potter |
| 3,595,228 A | 7/1971 | Simon et al. |
| 3,611,801 A | 10/1971 | Paine et al. |
| 3,659,604 A | 5/1972 | Melville et al. |
| 3,726,270 A | 4/1973 | Griffis et al. |
| 3,741,208 A | 6/1973 | Jonsson et al. |
| 3,783,893 A | 1/1974 | Davison |
| 3,802,417 A | 4/1974 | Lang |
| 3,817,246 A | 6/1974 | Weigl |
| 3,869,529 A | 3/1975 | Follette |
| 3,882,847 A | 5/1975 | Jacobs |
| 3,903,875 A | 9/1975 | Hughes |

(List continued on next page.)

FOREIGN PATENT DOCUMENTS

| | | |
|---|---|---|
| AU | B-59270/90 | 12/1990 |
| AU | A-62221/90 | 3/1991 |
| AU | A-33877/93 | 4/1993 |

(List continued on next page.)

OTHER PUBLICATIONS

Derwent: Flowmeter for fluids—has turbine transducer and volumetric sensor for simultaneous calibration.

Mark Kantrowitz, Erik Horskotte and Cliff Joslyn; "Answers to Frequently Asked Questions about Fuzzy Logic and Fuzzy Expert Systems" Version 1.24 last Modified 20 2 96.

New! Breas PV 100 CPAP First Class Quality and Function. At the right Price; Jul. 4, 1998, pp. 1–2.

(List continued on next page.)

Primary Examiner—John G. Weiss
Assistant Examiner—V. Srivastava
(74) Attorney, Agent, or Firm—Pillsbury Winthrop LLP

(57) ABSTRACT

An apparatus (10) for supplying breathable gas. The apparatus (10) includes a flow generator (12), a gas outlet (14), a connector (21) interposed between the flow generator (12) and the pressure sensor (20), the connector having a connecting inlet (22) and a connecting outlet (24), a pressure sensor (20) interposed between the connecting outlet (24) and the gas outlet (14). The connector (21) is adapted to allow selective connection to either a duct member (30) providing a direct flow path from the connecting inlet (22) to the connecting outlet (24) or to a humidifier (26) interposed between the connecting inlet (22) and the connecting outlet (24).

21 Claims, 7 Drawing Sheets

U.S. PATENT DOCUMENTS

| | | |
|---|---|---|
| 3,903,883 A | 9/1975 | Pecina et al. |
| 3,914,994 A | 10/1975 | Banner |
| 3,932,054 A | 1/1976 | McKelvey |
| 3,945,378 A * | 3/1976 | Paluch .................. 128/203.28 |
| 3,985,131 A * | 10/1976 | Buck et al. ............ 128/205.13 |
| 3,985,467 A | 10/1976 | Lefferson |
| 3,987,133 A | 10/1976 | Andra |
| 3,989,037 A | 11/1976 | Franetzki |
| 3,992,598 A | 11/1976 | Welsh et al. |
| 3,995,661 A | 12/1976 | Van Fossen |
| 4,006,634 A | 2/1977 | Billette et al. |
| 4,014,382 A | 3/1977 | Heath |
| 4,051,205 A | 9/1977 | Grant |
| 4,060,576 A | 11/1977 | Grant |
| 4,083,245 A | 4/1978 | Osborn |
| 4,109,749 A | 8/1978 | Sweet |
| 4,110,419 A | 8/1978 | Miller |
| 4,119,096 A | 10/1978 | Drews |
| 4,201,204 A | 5/1980 | Rinne et al. |
| 4,203,027 A | 5/1980 | O'Hare et al. |
| 4,206,754 A | 6/1980 | Cox et al. |
| 4,249,527 A | 2/1981 | Ko et al. |
| 4,251,027 A | 2/1981 | Dehart et al. |
| 4,301,833 A | 11/1981 | Donald, III |
| 4,312,235 A | 1/1982 | Daigle |
| 4,313,436 A * | 2/1982 | Schwanbom et al. .. 128/203.12 |
| 4,322,594 A | 3/1982 | Brisson |
| 4,346,048 A | 8/1982 | Gates |
| 4,351,327 A | 9/1982 | Rinne et al. |
| 4,381,788 A | 5/1983 | Douglas |
| 4,387,722 A | 6/1983 | Kearns |
| 4,389,353 A | 6/1983 | Gates |
| 4,389,901 A | 6/1983 | Lake |
| 4,396,034 A | 8/1983 | Cherniak |
| 4,414,982 A | 11/1983 | Durkan |
| 4,433,693 A | 2/1984 | Hochstein |
| 4,448,035 A | 5/1984 | Moriyama et al. |
| 4,448,058 A | 5/1984 | Jaffe et al. |
| 4,449,525 A | 5/1984 | White et al. |
| 4,481,944 A | 11/1984 | Bunnell |
| 4,499,914 A | 2/1985 | Schebler |
| 4,506,666 A | 3/1985 | Durkan |
| 4,507,976 A | 4/1985 | Banko |
| 4,519,399 A | 5/1985 | Hori |
| 4,530,334 A | 7/1985 | Pagdin |
| 4,550,615 A | 11/1985 | Grant |
| 4,550,726 A | 11/1985 | McEwen |
| 4,558,710 A | 12/1985 | Eichler |
| 4,570,631 A | 2/1986 | Durkan |
| 4,579,114 A | 4/1986 | Gray et al. |
| 4,580,575 A | 4/1986 | Birnbaum et al. |
| 4,590,772 A | 5/1986 | Nose et al. |
| 4,592,880 A | 6/1986 | Murakami |
| 4,595,016 A | 6/1986 | Fertig et al. |
| 4,595,139 A | 6/1986 | Levine |
| 4,602,644 A | 7/1986 | DiBenedetto et al. |
| 4,621,632 A | 11/1986 | Bartels et al. |
| 4,630,614 A | 12/1986 | Atlas |
| 4,648,396 A | 3/1987 | Raemer |
| 4,648,407 A | 3/1987 | Sackner |
| 4,649,755 A | 3/1987 | Volz |
| 4,655,213 A | 4/1987 | Rapoport et al. |
| 4,677,975 A | 7/1987 | Edgar et al. |
| 4,686,974 A | 8/1987 | Sato et al. |
| 4,686,999 A | 8/1987 | Snyder et al. |
| 4,688,433 A | 8/1987 | Sliverwater |
| 4,719,910 A * | 1/1988 | Jensen .................. 128/204.21 |
| 4,722,334 A * | 2/1988 | Blackmer et al. ...... 128/203.16 |
| 4,738,266 A | 4/1988 | Thatcher |
| 4,747,403 A | 5/1988 | Gluck et al. |
| 4,773,411 A | 9/1988 | Downs |
| 4,777,963 A | 10/1988 | McKenna |
| 4,790,194 A | 12/1988 | Bellows et al. |
| 4,790,832 A * | 12/1988 | Lopez .................. 128/207.18 |
| 4,795,314 A | 1/1989 | Prybella et al. |
| 4,796,651 A | 1/1989 | Ginn et al. |
| 4,802,485 A | 2/1989 | Bowers et al. |
| 4,803,471 A | 2/1989 | Rowland |
| 4,807,616 A * | 2/1989 | Adahan .................. 128/204.21 |
| 4,819,629 A | 4/1989 | Jonson |
| 4,823,788 A | 4/1989 | Smith et al. |
| 4,825,802 A | 5/1989 | Le Bec |
| 4,827,774 A | 5/1989 | Silverwater |
| 4,827,922 A | 5/1989 | Champain et al. |
| 4,829,998 A * | 5/1989 | Jackson .................. 128/204.18 |
| 4,838,258 A | 6/1989 | Dryden et al. |
| 4,844,085 A | 7/1989 | Gattinoni |
| 4,856,506 A | 8/1989 | Jinotti |
| 4,860,766 A | 8/1989 | Sackner |
| 4,870,960 A | 10/1989 | Hradek |
| 4,870,963 A | 10/1989 | Carter |
| 4,879,662 A | 11/1989 | Vicari et al. |
| 4,913,401 A | 4/1990 | Handke |
| 4,915,103 A | 4/1990 | Visveshwara et al. |
| 4,928,684 A | 5/1990 | Breitenfelder et al. |
| 4,934,397 A | 6/1990 | Niemela et al. |
| 4,938,210 A | 7/1990 | Shene |
| 4,938,212 A | 7/1990 | Gnook et al. |
| 4,944,310 A | 7/1990 | Sullivan |
| 4,957,107 A | 9/1990 | Sipin |
| 4,960,118 A | 10/1990 | Pennock |
| 4,971,065 A | 11/1990 | Pearce |
| 4,972,842 A | 11/1990 | Korten et al. |
| 4,982,738 A | 1/1991 | Griebel |
| 4,984,601 A | 1/1991 | Andersson et al. |
| 4,986,269 A | 1/1991 | Hakkinen |
| 4,989,599 A | 2/1991 | Carter |
| 4,993,269 A | 2/1991 | Guillaume et al. |
| 5,009,635 A | 4/1991 | Scarberry |
| 5,024,219 A | 6/1991 | Dietz |
| 5,033,311 A | 7/1991 | Custer |
| 5,033,312 A | 7/1991 | Stupecky |
| 5,038,621 A | 8/1991 | Stupecky |
| 5,046,491 A | 9/1991 | Derrick |
| 5,048,515 A | 9/1991 | Sanso |
| 5,052,400 A | 10/1991 | Dietz |
| 5,063,922 A | 11/1991 | Hakkinen |
| 5,063,938 A | 11/1991 | Beck et al. |
| 5,065,756 A | 11/1991 | Rapoport |
| 5,069,222 A | 12/1991 | McDonald, Jr. |
| 5,081,913 A | 1/1992 | Gervais |
| 5,099,837 A | 3/1992 | Russel, Sr. et al. |
| 5,105,354 A | 4/1992 | Nishimura |
| 5,107,830 A | 4/1992 | Younes |
| 5,107,831 A | 4/1992 | Halpern et al. |
| 5,117,819 A | 6/1992 | Servidio et al. |
| 5,125,753 A | 6/1992 | Ries et al. |
| 5,129,390 A | 7/1992 | Chopin et al. |
| 5,134,890 A | 8/1992 | Abrams |
| 5,134,995 A | 8/1992 | Gruenke et al. |
| 5,137,026 A | 8/1992 | Waterson et al. |
| 5,146,941 A | 9/1992 | Statler |
| 5,148,802 A | 9/1992 | Sanders et al. |
| 5,161,525 A | 11/1992 | Kimm et al. |
| 5,161,541 A | 11/1992 | Bowman et al. |
| 5,163,423 A | 11/1992 | Suzuki |
| 5,165,398 A | 11/1992 | Bird |
| 5,170,798 A | 12/1992 | Riker |
| 5,174,287 A | 12/1992 | Kallok et al. |
| 5,178,138 A | 1/1993 | Walstrom et al. |
| 5,183,983 A | 2/1993 | Knop |

| Patent | Date | Inventor |
|---|---|---|
| 5,187,988 A | 2/1993 | Dettmer et al. |
| 5,190,048 A | 3/1993 | Wilkinson |
| 5,195,528 A | 3/1993 | Hok |
| 5,199,424 A | 4/1993 | Sullivan et al. |
| 5,203,343 A | 4/1993 | Axe et al. |
| 5,230,330 A | 7/1993 | Price |
| 5,231,979 A | 8/1993 | Rose et al. |
| 5,231,983 A | 8/1993 | Matson et al. |
| 5,234,021 A | 8/1993 | Koziak et al. |
| 5,239,994 A | 8/1993 | Atkins |
| 5,239,995 A | 8/1993 | Estes et al. |
| 5,240,177 A | 8/1993 | Muramatsu et al. |
| 5,245,995 A | 9/1993 | Sullivan et al. |
| 5,259,373 A | 11/1993 | Gruenke et al. |
| 5,271,391 A | 12/1993 | Graves |
| 5,280,784 A | 1/1994 | Kohler |
| 5,293,864 A | 3/1994 | McFadden |
| 5,303,698 A | 4/1994 | Tobia et al. |
| 5,303,700 A | 4/1994 | Weismann et al. |
| 5,303,738 A | 4/1994 | Chang et al. |
| 5,305,787 A | 4/1994 | Thygesen |
| 5,311,875 A | 5/1994 | Stasz |
| 5,313,937 A | 5/1994 | Zdrojkowski |
| 5,316,261 A | 5/1994 | Stoner |
| 5,322,057 A | 6/1994 | Raabe et al. |
| 5,327,789 A | 7/1994 | Nijdam |
| 5,335,654 A | 8/1994 | Rapoport |
| 5,335,656 A | 8/1994 | Bowe et al. |
| 5,343,878 A | 9/1994 | Scarberry et al. |
| 5,353,788 A | 10/1994 | Miles |
| 5,360,008 A | 11/1994 | Campbell, Jr. |
| 5,363,857 A | 11/1994 | Howard |
| 5,367,604 A | 11/1994 | Murray |
| 5,373,842 A | 12/1994 | Olsson et al. |
| 5,388,571 A | 2/1995 | Roberts et al. |
| 5,394,882 A | 3/1995 | Mawhinney |
| 5,398,673 A | 3/1995 | Lambert |
| 5,400,777 A | 3/1995 | Olsson et al. |
| 5,404,758 A | 4/1995 | Huber et al. |
| 5,404,871 A | 4/1995 | Goodman et al. |
| 5,413,111 A | 5/1995 | Wilkinson |
| 5,433,193 A | 7/1995 | Sanders et al. |
| 5,438,980 A | 8/1995 | Phillips |
| 5,443,061 A | 8/1995 | Champain et al. |
| 5,443,075 A | 8/1995 | Holscher |
| 5,458,007 A | 10/1995 | Lake |
| 5,458,137 A | 10/1995 | Axe et al. |
| 5,479,920 A | 1/1996 | Piper et al. |
| 5,483,969 A | 1/1996 | Testerman et al. |
| 5,488,969 A | 2/1996 | King et al. |
| 5,490,502 A | 2/1996 | Rapoport et al. |
| 5,492,113 A | 2/1996 | Estes et al. |
| 5,503,146 A | 4/1996 | Froehlich et al. |
| 5,507,282 A | 4/1996 | Younes |
| 5,509,404 A | 4/1996 | Lloyd et al. |
| 5,509,414 A | 4/1996 | Hok |
| 5,513,631 A | 5/1996 | McWilliams |
| 5,517,983 A | 5/1996 | Deighan et al. |
| 5,522,382 A | 6/1996 | Sullivan et al. |
| 5,526,805 A | 6/1996 | Lutz et al. |
| RE35,295 E | 7/1996 | Estes et al. |
| 5,532,922 A | 7/1996 | Wacker et al. |
| 5,535,738 A | 7/1996 | Estes et al. |
| 5,535,739 A | 7/1996 | Rapoport et al. |
| 5,537,997 A | 7/1996 | Mechlenburg et al. |
| 5,540,219 A | 7/1996 | Mechlenburg et al. |
| 5,540,220 A | 7/1996 | Gropper |
| 5,540,733 A | 7/1996 | Testerman et al. |
| 5,546,933 A | 8/1996 | Rapoport et al. |
| 5,546,952 A | 8/1996 | Erickson |
| 5,549,106 A | 8/1996 | Gruenke et al. |
| 5,549,655 A | 8/1996 | Erickson |
| 5,551,418 A | 9/1996 | Estes et al. |
| 5,551,419 A | 9/1996 | Froehlich et al. |
| 5,558,084 A | 9/1996 | Daniell et al. |
| 5,558,099 A | 9/1996 | Bowman et al. |
| RE35,339 E | 10/1996 | Rapoport |
| 5,564,415 A | 10/1996 | Dobson et al. |
| 5,564,432 A | 10/1996 | Thomson |
| 5,567,127 A | 10/1996 | Wentz |
| 5,570,682 A | 11/1996 | Johnson |
| 5,588,439 A | 12/1996 | Hollub |
| 5,590,644 A | 1/1997 | Rosenkoetter |
| 5,590,648 A | 1/1997 | Mitchell |
| 5,598,837 A | 2/1997 | Sirianne, Jr. et al. |
| 5,598,838 A | 2/1997 | Servidio et al. |
| 5,605,151 A | 2/1997 | Lynn |
| 5,608,647 A | 3/1997 | Rubsamen et al. |
| 5,617,846 A | 4/1997 | Graetz et al. |
| 5,630,411 A | 5/1997 | Holscher |
| 5,632,269 A | 5/1997 | Zdrojkowski |
| 5,633,552 A | 5/1997 | Lee et al. |
| 5,642,730 A | 7/1997 | Baran |
| 5,645,053 A | 7/1997 | Remmers et al. |
| 5,645,054 A | 7/1997 | Cotner et al. |
| 5,647,351 A | 7/1997 | Wesimann et al. |
| 5,655,520 A | 8/1997 | Howe et al. |
| 5,655,522 A | 8/1997 | Mechlenburg et al. |
| 5,660,171 A | 8/1997 | Kimm et al. |
| 5,666,946 A | 9/1997 | Langenback |
| 5,673,687 A | 10/1997 | Dobson et al. |
| 5,682,878 A | 11/1997 | Ogden |
| 5,685,296 A | 11/1997 | Zdrojkowski et al. |
| 5,701,883 A | 12/1997 | Hete et al. |
| 5,704,345 A | 1/1998 | Berthon-Jones |
| 5,715,812 A | 2/1998 | Deighan et al. |
| 5,730,121 A | 3/1998 | Hawkins et al. |
| 5,740,795 A | 4/1998 | Brydon |
| 5,794,615 A | 8/1998 | Estes |
| 5,797,852 A | 8/1998 | Karakasoglu et al. |
| 5,803,066 A | 9/1998 | Rapoport et al. |
| 5,823,187 A | 10/1998 | Estes et al. |
| 5,832,917 A * | 11/1998 | Sarela et al. ............ 128/203.12 |
| 5,845,636 A | 12/1998 | Gruenke et al. |
| 5,918,596 A * | 7/1999 | Heinonen ............... 128/204.22 |
| 6,050,260 A * | 4/2000 | Daniell et al. ...... 128/204.22 X |

FOREIGN PATENT DOCUMENTS

| | | |
|---|---|---|
| AU | A-38508/93 | 7/1993 |
| AU | A-52628/93 | 7/1994 |
| AU | B 79174/94 | 6/1995 |
| AU | 9226120 | 7/1995 |
| AU | A-40711-95 | 4/1996 |
| AU | B 34354/95 | 5/1996 |
| AU | A 39130/95 | 6/1996 |
| DE | 3015279 A1 | 10/1981 |
| DE | 34 02 603 A1 | 8/1985 |
| DE | 3537507 A1 | 4/1987 |
| DE | 3539073 A1 | 5/1987 |
| EP | 0 062 166 A2 | 10/1982 |
| EP | 0 066 451 A1 | 12/1982 |
| EP | B1 0 088 761 | 9/1983 |
| EP | 0 164 500 A2 | 3/1985 |
| EP | 0 185 980 | 7/1986 |
| EP | 0 236 850 A2 | 9/1987 |
| EP | 0 872 643 A2 | 3/1988 |
| EP | 0 298 367 A2 | 1/1989 |
| EP | 0 330 459 | 8/1989 |
| EP | 0 425 092 A1 | 9/1989 |
| EP | 0 452 001 A2 | 3/1990 |
| EP | 0 388 525 A1 | 9/1990 |
| EP | 0 461 281 A1 | 12/1991 |

| | | |
|---|---|---|
| EP | 0 481 459 A1 | 4/1992 |
| EP | 0 535 952 A1 | 4/1993 |
| EP | 0549299 A2 | 6/1993 |
| EP | 606 687 A2 | 7/1994 |
| EP | 0651971 A1 | 5/1995 |
| EP | 0 656 216 A2 | 6/1995 |
| EP | 0 661 071 A1 | 7/1995 |
| EP | 178 925 A2 | 4/1996 |
| EP | 0 709 107 A1 | 5/1996 |
| EP | 0 714 670 A2 | 6/1996 |
| EP | 0 765 631 A2 | 4/1997 |
| EP | 0 788 805 A2 | 8/1997 |
| EP | 0 839 545 A1 | 5/1998 |
| EP | 0 845 277 | 6/1998 |
| FR | 2 672 221 | 8/1992 |
| FR | 2682042 A1 | 4/1993 |
| GB | 1 294 808 | 11/1972 |
| GB | 1432572 | 4/1976 |
| GB | 1 444 053 | 7/1976 |
| GB | 1583273 | 1/1981 |
| GB | 2 077 444 A | 12/1981 |
| GB | 2 087 570 A | 5/1982 |
| GB | 2 147 506 A | 5/1985 |
| GB | 2 164 421 A | 3/1986 |
| GB | 2 166 871 A | 5/1986 |
| GB | 2 205 167 A | 11/1988 |
| GB | 2 221 302 A | 1/1990 |
| GB | 2 223 593 A | 4/1990 |
| GB | 2 254 700 A | 10/1992 |
| GB | 2 261 290 A | 5/1993 |
| GB | 2 271 811 A | 4/1994 |
| GB | 2 294 400 A | 5/1996 |
| JP | 54-104369 | 8/1979 |
| JP | 60-212607 | 10/1985 |
| JP | 62-103297 | 4/1987 |
| JP | 63-275352 | 11/1988 |
| JP | 2-173397 | 12/1988 |
| JP | 4-70516 A | 3/1992 |
| JP | 4-70516 | 3/1992 |
| JP | 6-249742 A | 9/1994 |
| JP | 07280609 A | 10/1995 |
| SE | 1710064 A1 | 2/1992 |
| SE | 467041 B | 5/1992 |
| WO | WO 80/01044 | 5/1980 |
| WO | WO 82/03326 | 10/1982 |
| WO | WO 82/03548 | 10/1982 |
| WO | WO 86/05965 | 10/1986 |
| WO | WO 86/06969 | 12/1986 |
| WO | WO 87/02577 | 5/1987 |
| WO | WO 88/10108 | 12/1988 |
| WO | WO 90/14121 | 1/1990 |
| WO | WO 91/12051 | 8/1991 |
| WO | WO 92/11054 | 7/1992 |
| WO | WO 92/15353 | 9/1992 |
| WO | WO 92/22244 | 12/1992 |
| WO | WO 93/08857 | 5/1993 |
| WO | WO 93/09834 | 5/1993 |
| WO | WO 93/21982 | 11/1993 |
| WO | WO 93/24169 | 12/1993 |
| WO | WO 94/04071 | 3/1994 |
| WO | WO 94/16759 | 8/1994 |
| WO | WO 94/20018 | 9/1994 |
| WO | WO 94/20051 | 9/1994 |
| WO | WO 94/22517 | 10/1994 |
| WO | WO 94/23780 | 10/1994 |
| WO | WO 95/32016 | 11/1995 |
| WO | WO 96/16688 | 6/1996 |
| WO | WO 96/32055 | 10/1996 |
| WO | WO 96/35911 | 11/1996 |
| WO | WO 96/36279 | 11/1996 |
| WO | WO 96/40337 | 12/1996 |
| WO | WO 96/41571 | 12/1996 |
| WO | WO 97/02064 | 1/1997 |
| WO | WO 97/05824 | 2/1997 |
| WO | WO 97/10019 | 3/1997 |
| WO | WO 97/10868 | 3/1997 |
| WO | WO 97/15343 | 5/1997 |
| WO | WO 97/18752 | 5/1997 |
| WO | WO 97/20499 | 6/1997 |
| WO | WO 97/22377 | 6/1997 |
| WO | WO 97/28838 | 8/1997 |
| WO | WO 97/41812 | 11/1997 |
| WO | 98 04311 | 2/1998 |
| WO | WO 98/06449 | 2/1998 |
| WO | WO 98/25662 | 6/1998 |
| WO | WO 98/33433 | 8/1998 |
| WO | WO 98/35715 | 8/1998 |
| WO | WO 98/36245 | 8/1998 |
| WO | WO 98/36338 | 8/1998 |
| WO | WO 98/47554 | 10/1998 |
| WO | WO 98/57691 | 12/1998 |
| WO | 99 22793 | 5/1999 |
| WO | 00 27457 | 5/2000 |

OTHER PUBLICATIONS

PV 101 Bi Level CPAP and PV 102 Bi–Level Time; pp. 1–3.
Prodigy Medical Supplies Co. Ltd.; CPAP.
Puritan Bennett; Companion 318 Nasal CPAP System; 5/93.
Nellcor Puritan Bennett; Announcing the Goodnight 314 and GoodKnight 318 Nasal CPAP Systems.
Puritan Bennett; Clean, Quiet, and Comfortable . . . The Companion's 515 Nasal CPAP System; 6/88.
DeVilbiss Night Guard Nasal CPAP for the Treatment of Obstructive Sleep Apnea.
Sunrise; DeVilbiss Horizon LT 8001 Nasal CPAP Therapy Small in Size, big on features; 8/97.
Devilbiss; Revitalizer Soft Start; The Facts Speak for Themselves, 1992.
Tranquility; Performance CPAP Advantage.
Healthdyne International; Tranquility Plus.
Respironics Inc.; Respironics'Solo CPAP System Provides Simplified OSA Therapy at an Outstanding value; Sep. 19, 1996.
Respironics Inc.; The First Family of OSA Therapy; 1991.
Fisher & Paykel Healthcare; HC200 Series Nasal CPAP Blower & Heated Humidifier.
Pierre Medical; Morphee Plus appareil de traiment des apnees du sommeil manuel d'utilisation.
Weinmann:Hamburg; Somnotron nCPAP—Great WM 2300, 11/91.
Puritan Bennett; 515a Part of Our Blueprint for the Future; 3/90.
Puritan Bennett; Companion 320 I/E Bi–Level Respiratory System; 4/93.
ResMed; Sullivan VPAP II & II ST.
ResMed; The Sullivan V Family of CPAP Systems; 1996.
ResMed; The AutoSet Portable II; 1997.
ResMed; Sullivan Nasal CPAP System.
ResMed; The Sullivan IIID; 1995.
ResMed; The Sullivan Comfort; 1996.
DeVilbiss a Division of Sunrise Medical; Expand your Horizons With The Horizons; 1995.
Healthdyne Technologies; Home Health Care Dealer; The Journal of Home Medical Equipment and Services/Supplier; Nov. and Dec. 1997.
Healthdyne International; Tranquility Quest, The Compact CPAP for Greater patient comfort.

AirStep; Medical Products . . . Stand the Test of Time.

MAP Medical Progress for Physician und Patient; The Gentle Therapy for Sleep–Related Breathing Disorders.

Taema; Ventilation CP 90.

DPAP; Breath, by breath, by breath.

Lifecare; Smallest. Quietest. Smartest.

Lifecare; Quiet CPAP System for Maximum Compliance; 1991.

Lifecare; Software Nasal Mask, Custom Nasal Masks; 1991.

Nidek Medical; Silenzio.

Weinmann; Just to Fell Well, Sensitive Sleep Apnea Therapy with Somnotron 3 and Somno–Mask System.

Respironics Inc.; Aria CPAP System; 1993.

Respironics Inc.; SleepEasy III A New Dawn in Patient Compliance.

Respironics Inc.; Muliple Choice REMstar Choice Nasal CPAP System.

Maxll nCPAP and Moritz II Bi–Level Brochure.

* cited by examiner

APPARATUS FOR SUPPLYING BREATHABLE GAS

FIELD OF THE INVENTION

The present invention relates to an apparatus for supplying breathable gas.

The present invention has been developed primarily for use in Continuous Positive Airway Pressure (CPAP) treatment of, for example, Obstructive Sleep Apnea (OSA) in which pressurised air is supplied to a patient's airways to pneumatically splint them open. The pressure of the gas supplied to the patient can be constant, bi-level (in synchronism with patient breathing) or auto-setting in level. Throughout this specification any reference to CPAP is intended to incorporate a reference to any one of, or combinations of, these forms of pressurised gas supply.

The invention is also suitable for supplying gas for assisted respiration or mechanical ventilation.

BACKGROUND OF THE INVENTION

Some people find breathing the cool, dry air produced by the flow generator of a gas supplying apparatus uncomfortable, leading to possible lack of treatment compliance. It can also cause a dry or runny nose. This problem can be ameliorated by placing a humidifier in the gas flow path between the flow generator and the patient to moisturize the gas supplied to the patient. A humidifier basically is a reservoir of water over the surface of which the pressurised breathable gas flows. The water can be heated (known as an "active" humidifier) or unheated (known as "passive").

In some gas supply apparatus, in particular those used in CPAP treatment, it is desirable or necessary to monitor the pressure of the gas being supplied at the mask worn on the patient's face. This is generally done by monitoring the pressure at the flow generator with an electronic pressure transducer and then compensating for the known flow characteristics of the delivery tube and mask by calibration to determine the mask treatment pressure.

However, if a humidifier is placed between the flow generator and the mask (downstream of the pressure transducer) its pneumatic impedance of the gas flow may result in large pressure swings and the introduction of errors into the mask pressure calculation. Moreover, if the pressure signal is used to measure snore as an indication of partial apnea, the humidifier may muffle the snore component thereby reducing the accuracy of the snore measurement.

It is known to ameliorate these problems by using a hollow cylindrical plug having a pressure sensing port connected by a flexible tube to a pressure transducer mounted within the housing that contains the flow generator. If the apparatus is used without a humidifier the plug has one end connect directly to the flow generator outlet and the other connected to the mask supply tube inlet. When a humidifier is used, the humidifier inlet is connected to the flow generator outlet and the humidifier outlet is connected to one end of the plug. The other end of the plug remains connected to the mask supply tube inlet. In this way, the pressure monitored by the pressure transducer is downstream of the humidifier and not affected by its alteration of the gas supply path.

However, this apparatus suffers from several problems. Firstly, the usage of the plug and associated tube is messy and unsightly. Further, the tube is thin and prone to kinking and/or squashing leading to inaccuracies in pressure measurement, Also, if the tube is removed and inadvertently replaced with a tube of different length or diameter, the accuracy of the mask pressure calculation is adversely affected. Finally, the apparatus suffers from the possibility that the humidifier or plug may be incorrectly installed, particularly when used by patients in the home and/or with humidifiers manufactured by a third party.

The above disadvantages may be ameliorated by incorporating a humidifier into the housing that contains the flow generator. However, this is uneconomical as many patients do not require this feature.

Accordingly, there exists a need for an apparats for supplying breathable gas which can be easily and simply connected to a humidifier and which may also be quickly and simply configured to function without a humidifier, in which gas supply pressure is sensed downstream of the humidifier, if present.

The present invention is directed towards achieving one or more of these needs and, in particular, to substantially overcoming or at least ameliorating one or more of the disadvantages of the existing apparatus described above.

SUMMARY OF THE INVENTION

Accordingly, in the first aspect, the present invention discloses an apparatus for supplying breathable gas, the apparatus includes:

a flow generator;

a gas outlet;

a connection mans interposed between the flow generator and the gas outlet, the connection means having a connection inlet and a connection outlet; and a pressure sensing means interposed between the connection outlet and the gas outlet, wherein the connection means is adapted to allow selective connection to either a duct member providing a direct flow path from the connection inlet to the connection outlet or to a humidifier interposed between the connection inlet and the connection outlet.

The connection inlet receives gas from the flow generator. The connection outlet receives gas from the humidifier or the duct member, as the case may be.

Preferably, the breathable gas is air,

Desirably, the apparatus is connected by a gas supply tube to a patient "mask" to provide CPAP treatment, assisted respiration or mechanical ventilation. Mask varieties include nose masks, mouth masks, combination nose and mouth masks, nasal prongs, nasal pillows and fill face masks.

The pressure sensing means is preferably an electronic pressure transducer.

The connection inlet and the connection outlet may be identical or may be different, for example in cross-sectional shape or diameter, in order to avoid incorrect installation of the duct member or the humidifier.

Preferably, the connection inlet and the connection outlet are recessed behind the outer edge of the casing or housing of the apparatus. In an embodiment, the duct member is in the form of a substantially U-shaped pipe adapted to connect the connection inlet and the connection outlet, The pipe preferably has an outer panel attached thereto which, upon installation, is substantially flush with adjacent outer panels of the casing or housing. In a preferred form the U-shaped pipe is comprised of two joined sections encased in a shape having a snap-engageable base and lid.

The humidifier can include a heater (ie. active) or be unheated (ie. passive).

In an embodiment, the apparatus also includes a gas flow rate sensing means interposed between the connection outlet and the gas outlet. In one form, the gas flow rate sensing means is a pressure differential flow sensor communicating with two pressure ports, the ports being respectively disposed on opposite sides of a flow impedance. In a preferred form, one of the pressure ports, preferably the port closest to the gas outlet, also communicates with the pressure sensing means.

The duct-member, and other components in the gas path, are desirably produced from antimicrobial materials. The duct member, and other components in the gas path, are also desirably disposable.

In a second aspect, the present invention discloses a CPAP treatment device incorporating the apparatus of the first aspect.

BRIEF DESCRIPTION OF THE DRAWINGS

A preferred embodiment of the invention will now be described, by way of example only, with reference to the accompanying drawings in which.

DETAILED DESCRIPTION OF THE PREFERRED EMBODIMENT

Figure 1:
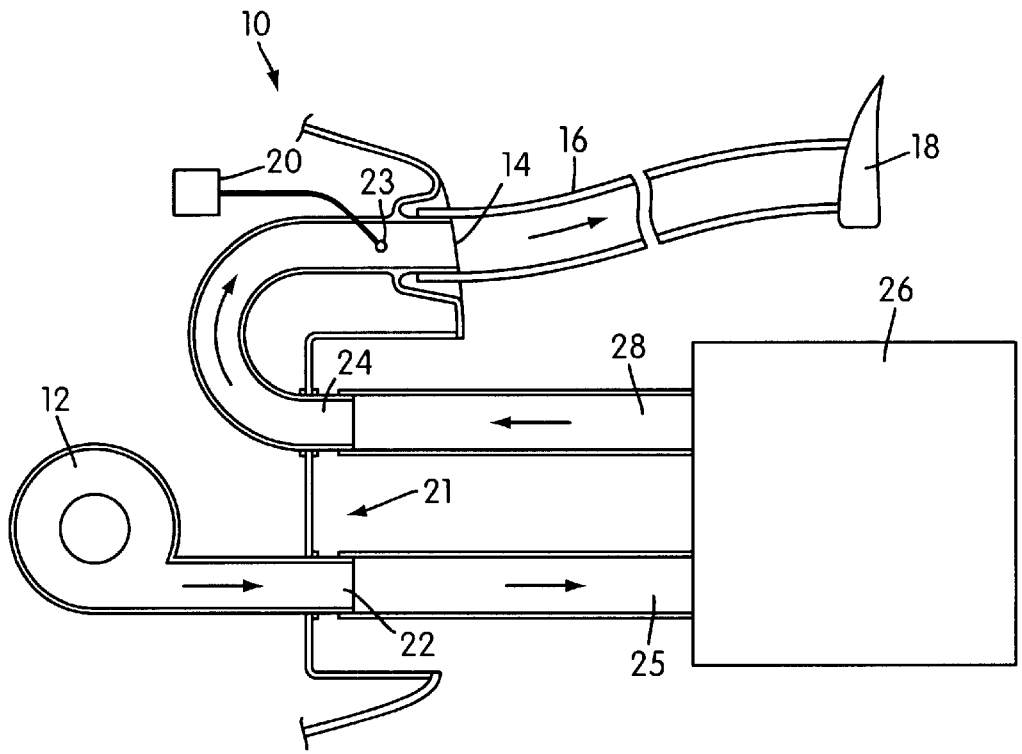
FIG. 1 is a partial sectional schematic plan view of a first embodiment of a breathable gas supply apparatus according to the invention connected to a humidifier.
Figure 2:
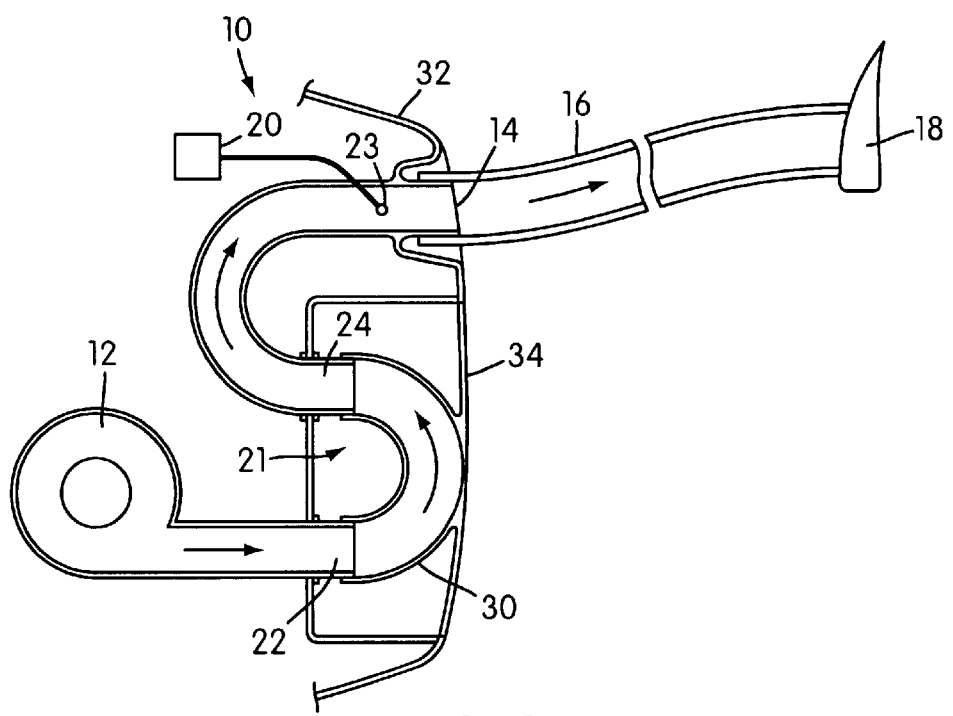
FIG. 2 is a view similar to FIG. 1, but showing the apparatus connected to a duct member.

Referring to the FIGS. 1 and 2, there is partially shown a first embodiment of an apparatus 10 for supplying breathable gas according to the invention. The apparatus 10 includes a flow generator 12 and a breathable gas outlet 14. The breathable gas outlet 14 is connected by a flexible gas supply tube 16 to a face mask 18 worn by a patient (not shown). A connection means, indicated generally at 21, is disposed between the pressure transducer 20 and the flow generator 12 and includes a connection inlet 22 and a connection outlet 24. A pressure sensing means, in the form of a pressure transducer 20 connected to a port tapping 23, is disposed between the connection outlet 24 the gas outlet 14.

In FIG. 1, the connection inlet 22 is shown connected to the inlet tube 25 of a humidifier 26. The connection outlet 24 is connected to the outlet tube 28 of the humidifier 26. Thus, the pressure transducer 20 measures the gas supply pressure downstream of the humidifier 26 and is not affected any pneumatic impedance it introduces.

In FIG. 2, the apparatus 10 is shown configured without the humidifier 26. In this configuration, a duct member in the form of a substantially U-shaped pipe 30 provides a direct gas flow path from the connection inlet 22 to the connection outlet 24.

The main advantages of the apparatus are two-fold. Firstly, if a humidifier is used, gas supply pressure is measured downstream thereof and thus includes any pressure swings or variations introduced by the humidifier. Secondly, the apparatus can be quickly and easily converted between including, or not including, a humidifier in the gas supply path.

In the embodiment shown, the inlet 22 and outlet 24 are recessed behind the external boundary of the casing or housing 32 of the apparatus 10. The duct member 30 includes a panel 34 which, upon installation, is substantially flush with the casing 32 thereby providing a neat appearance to the apparatus 10.

Figure 3:
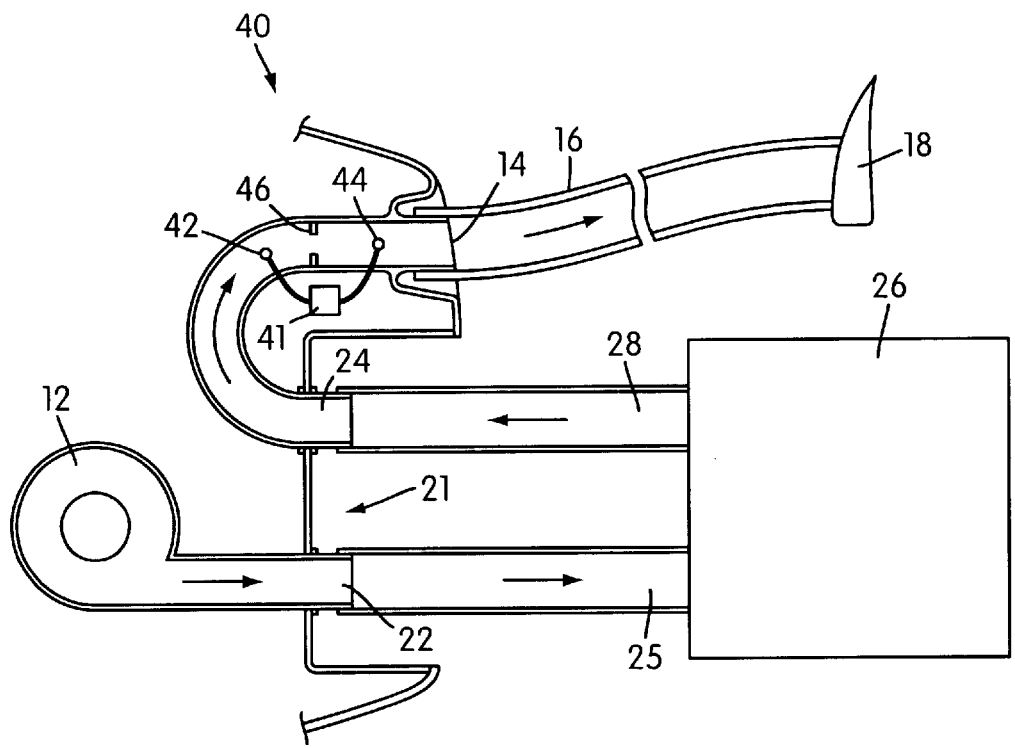
FIG. 3 is a partial sectional schematic plan view of a second embodiment of a breathable gas supply apparatus according to the invention connected to a humidifier.
Figure 4:
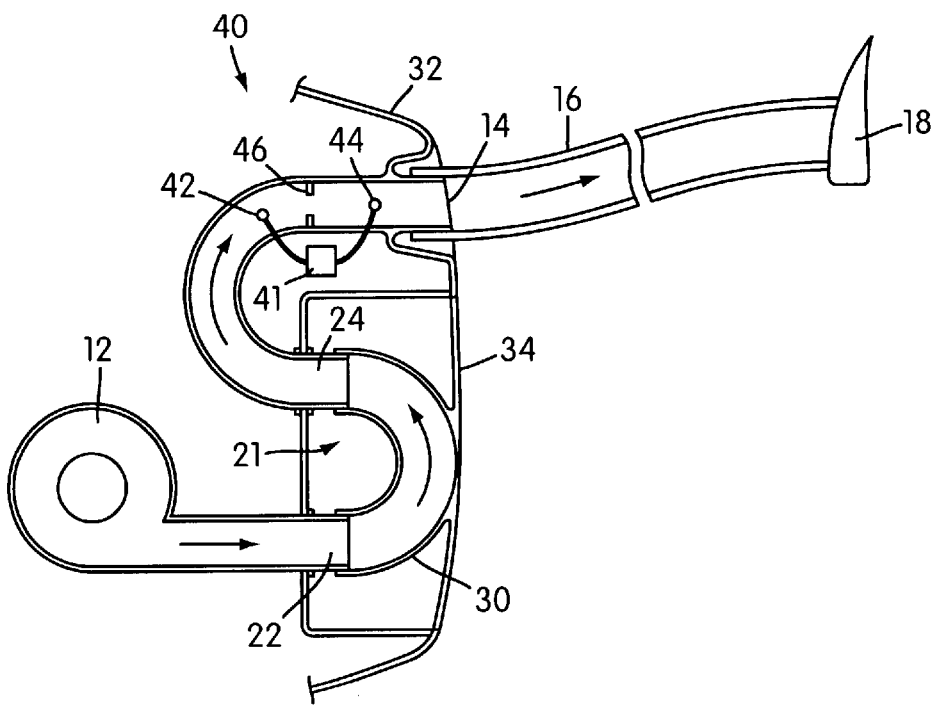
FIG. 4 is a view similar to FIG. 3, but showing the apparatus connected to a duct member.

FIGS. 3 and 4 show a second embodiment of an apparatus 40 for supplying breathable gas according to the invention. Like reference numerals to those used in describing the first embodiment will be used to denote like feature with respect to the second embodiment.

The apparatus 40 includes a gas flow rate sensing means in the form of a pressure differential flow sensor 41 communicated with pressure tappings 42 and 44 provided either side of a flow impeding orifice 46.

Flow impedance can also be accomplished by providing a straw bundle, flexible membrane, vortex former or the like between the tappings 42 and 44.

Pressure measurement can be performed by using a separate pressure sensing means (not shown), such as the pressure transducer 20 and the tapping 23 from the first embodiment or by measuring the pressure at one of the ports 42 or 44. The port 44 is preferable because it is closer to the gas supply conduit 16.

FIGS. 5 to 8 show a third embodiment of an apparatus 60 for supplying breathable gas according to the invention. Like reference numerals to those used in describing the first embodiment will again be used to denote like features with respect to the third embodiment.

Figure 5:
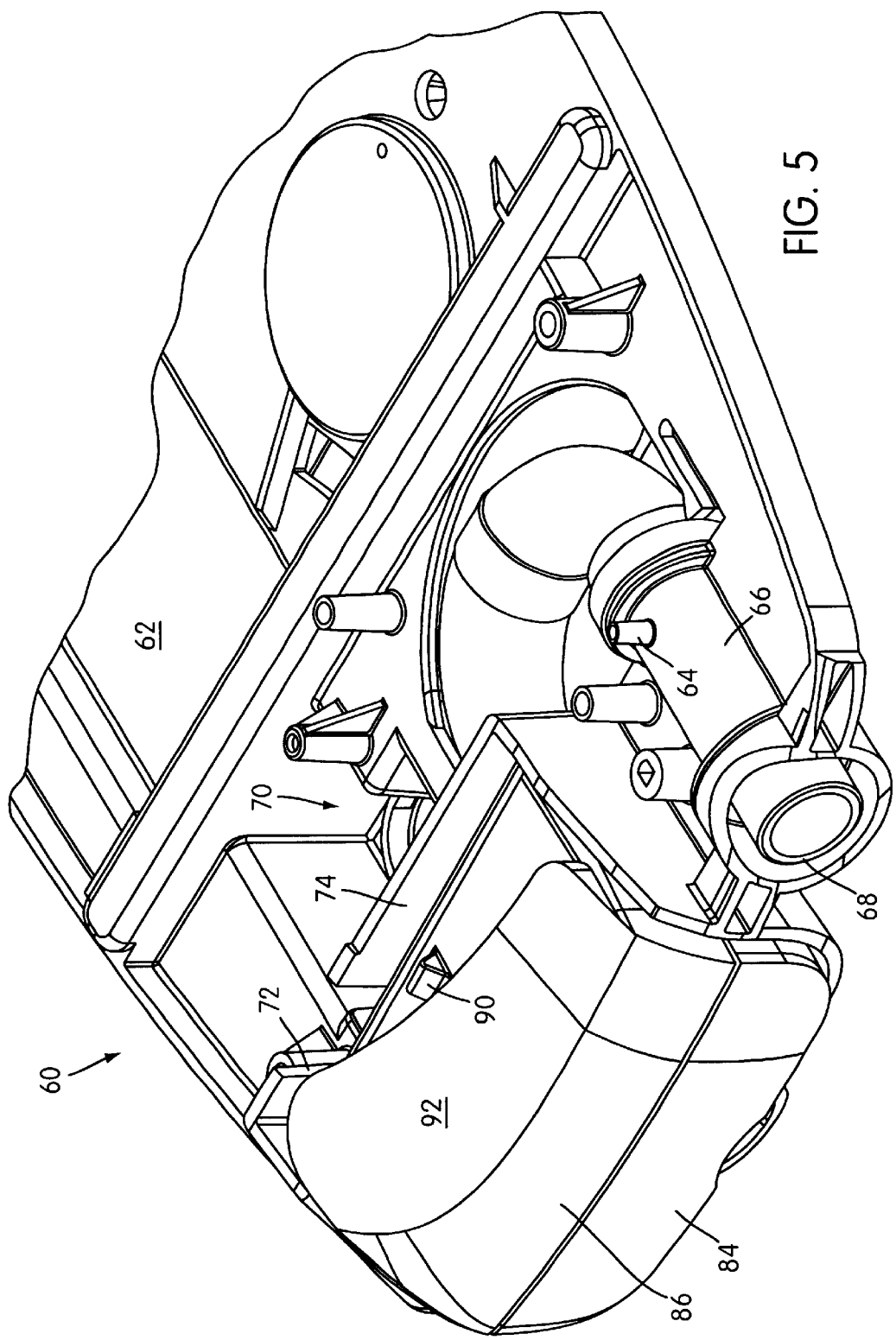
FIG. 5 is a partial perspective view of the chassis of a third embodiment of a gas supply apparatus according to the invention connected to a duct member.
Figure 6:
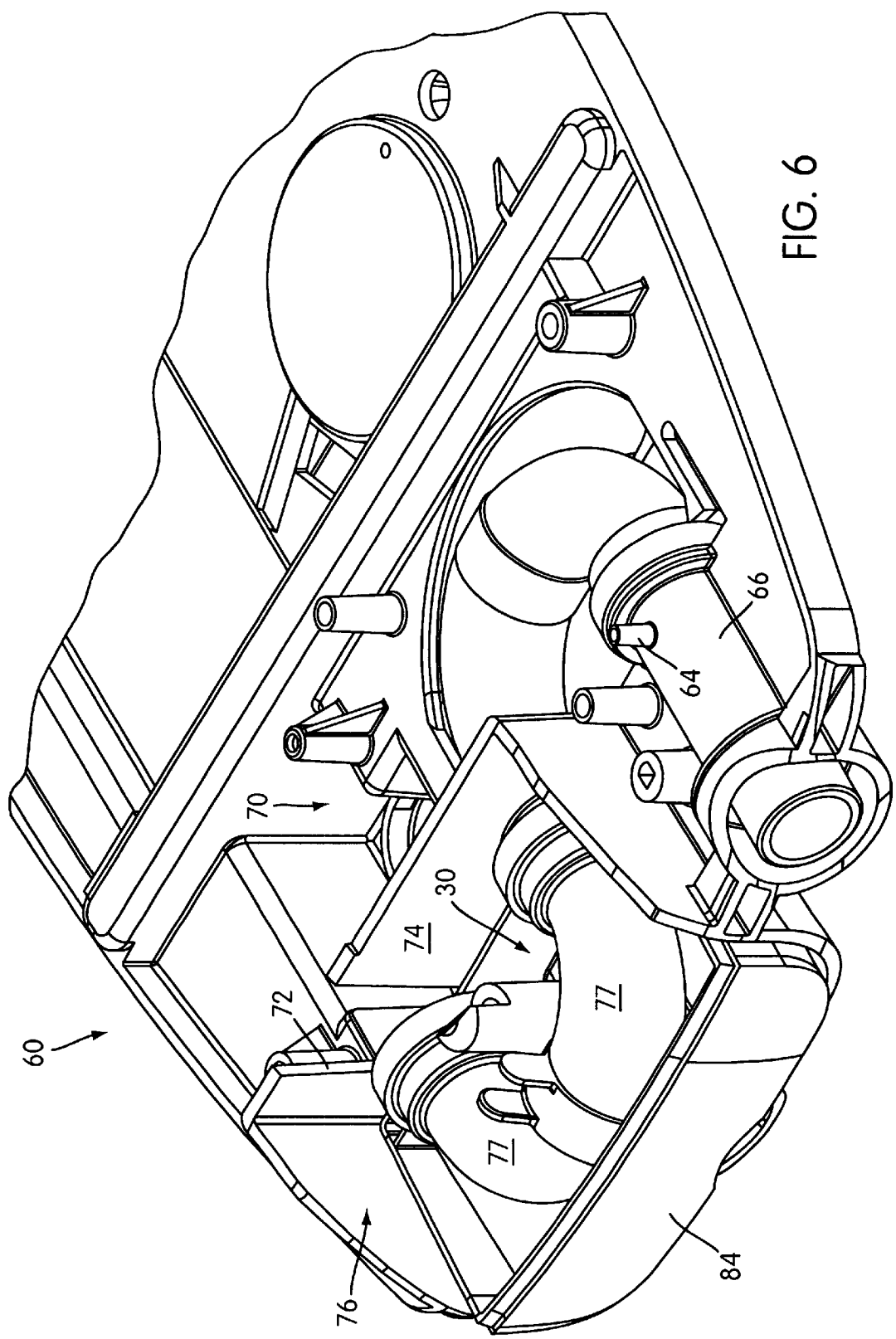
FIG. 6 is a view similar to FIG. 5 with the lid of the duct member removed.
Figure 7:
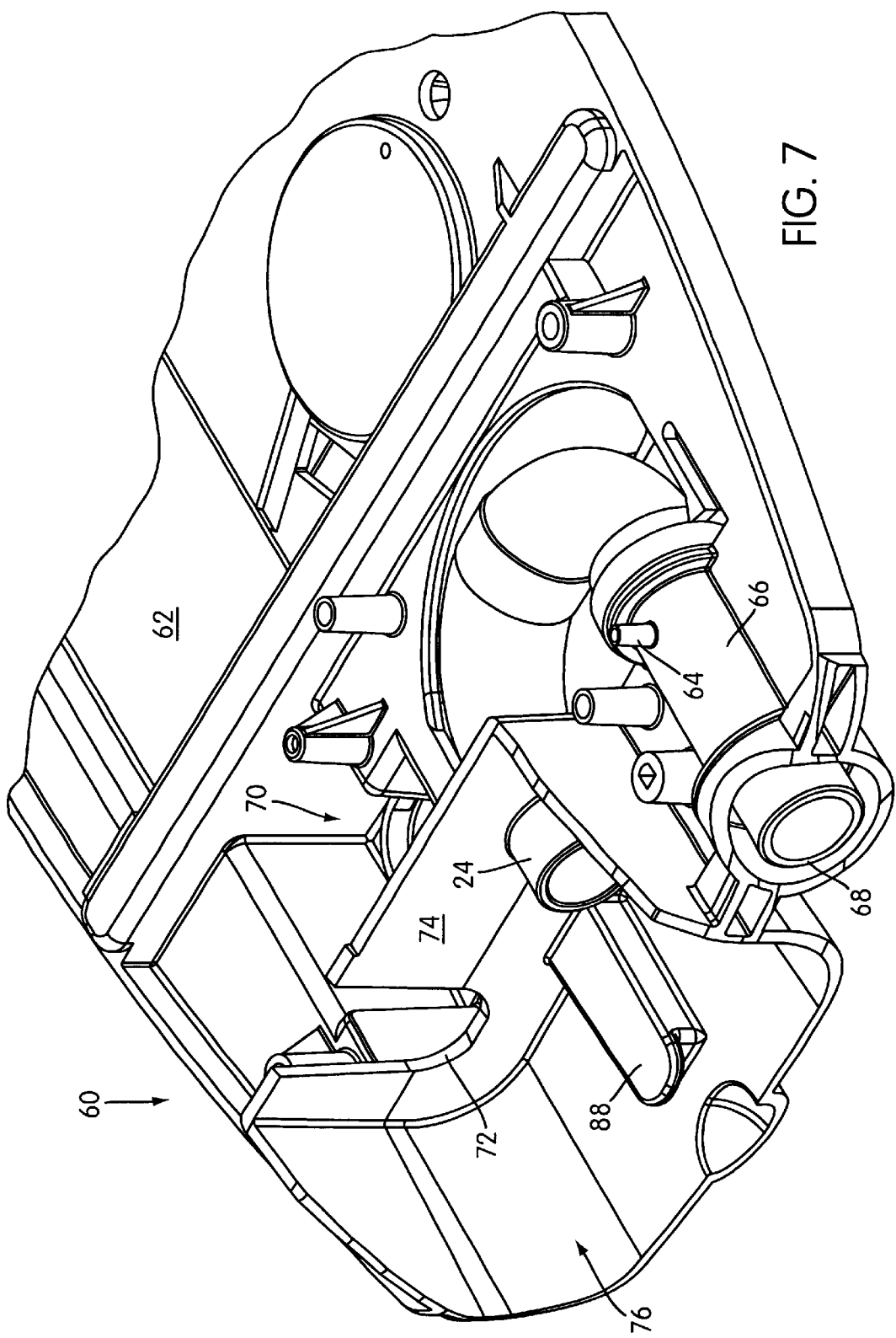
FIG. 7 is a view similar to FIG. 5 with the duct member removed.
Figure 8:
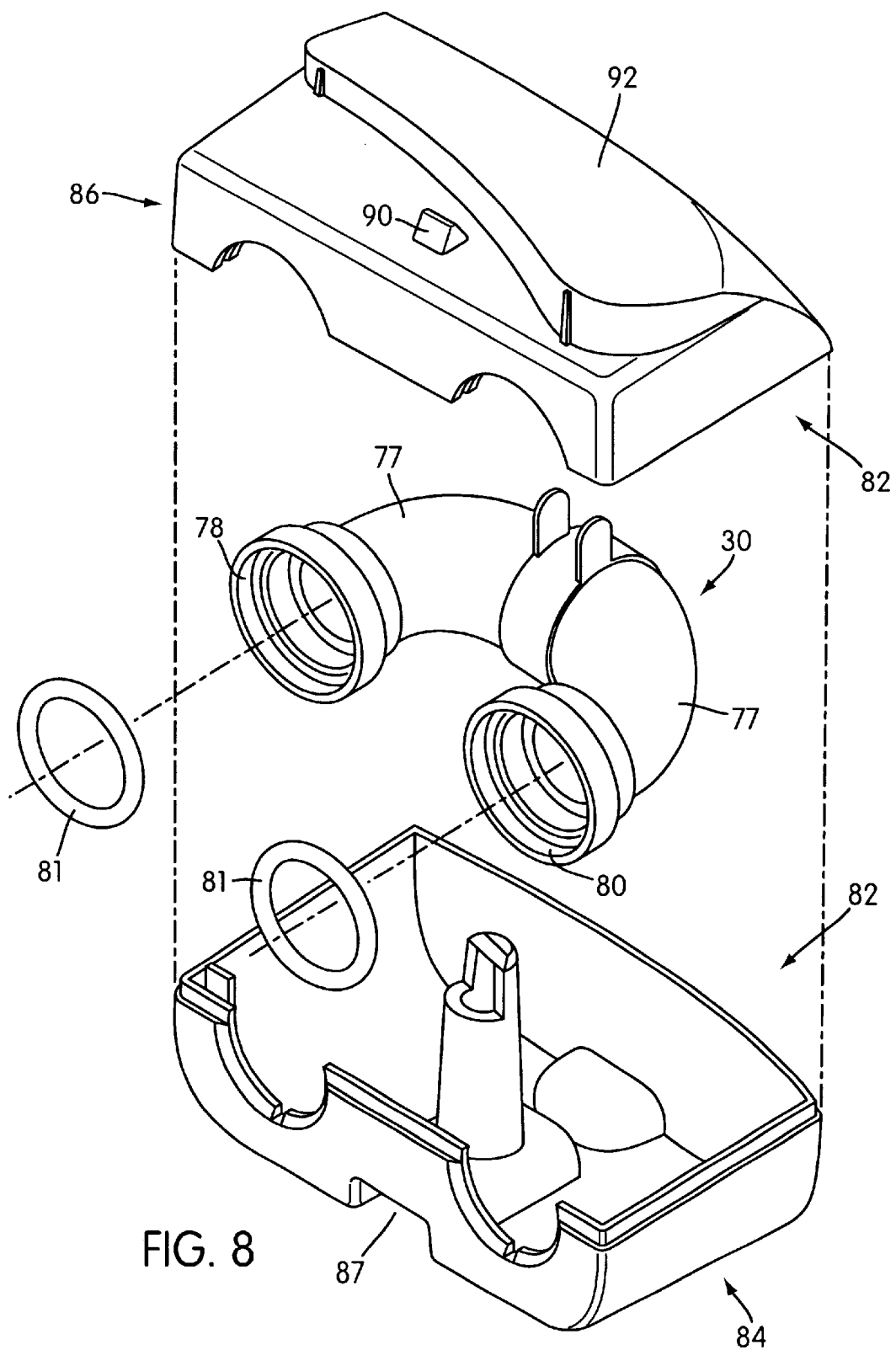
FIG. 8 is an exploded perspective view of the duct member shown in FIG. 5.

FIGS. 5 to 7 show a mounting chassis 62 of the apparatus 60 with the upper external lid or cover removed. A pressure transducer (not shown) communicates with the supplied gas at port 64 provided in outlet tube 66. The tube 66 terminates in spigot 68 which is adapted for connecting to the gas supply conduit (not shown).

The chassis 62 includes a recess at 70 fiber filament of a flow meter (not shown) includes a gas outlet in the form of a cylindrical tube which is positionable to protrude through U-shaped cut-out 72 (see FIG. 7) to constitute the connection inlet in a similar manner to the connection outlet 24 shown protruding from back wall 74 of chassis recess 76.

In this embodiment, the duct member 30 is comprised of two ABS plastic 90° tubes 77 connected by a DYNAFLEX (Trade Mark) thermoplastic elastomer connector produced by the GLS Corporation of OHIO, USA. Ends 78 and 80 of the duct member 30 include silicone 'O'-rings 81 coated with paralene. The duct member 30 is mounted within a box 82 comprising a base 84 and a lid 86 which are adapted to snap engage with one another.

The base 84 includes a recess 87 for engaging a tongue 88 (see FIG. 7) provided in chassis recess 70 to correctly position the box 82. The lid 86 includes a protuberance 90 which snap engages a complimentary recess in the lid (not shown) of the apparatus 60 to retain the box 82 adjacent the chassis 62. The curved upper surface 92 of the box is a smooth continuation of We adjacent upper surface of die apparatus lid.

The U-shaped member 30 and the box 82 can be produced from an antimicrobial material or be disposable to reduce the risk of infection between different users of the apparatus 60. Other components in the gas path, such as the outlet tube 66, can also be made from antimicrobial material or be disposable.

FIGS. 5 and 6 show the apparatus 60 configured for use without a humidifier. FIG. 7 shows the apparatus 60 in a configuration suitable for connection to the inlet and outlet tubes of a humidifier (after installation of the aforementioned flow sensor).

Figure 9:
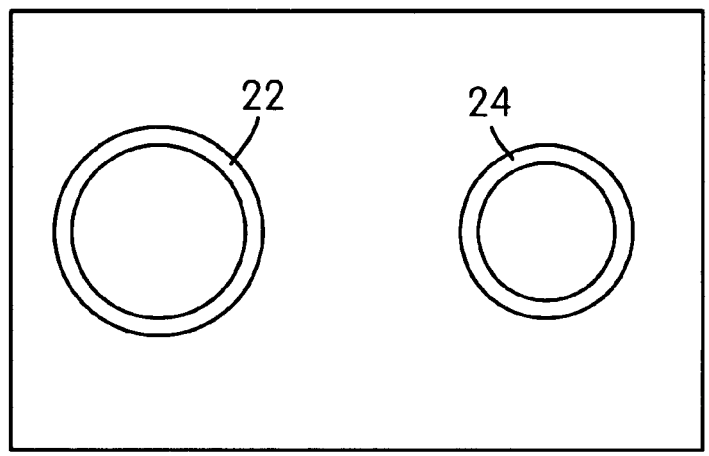
FIG. 9 is a schematic front view of another embodiment of the connection inlet and outlet.
Figure 10:
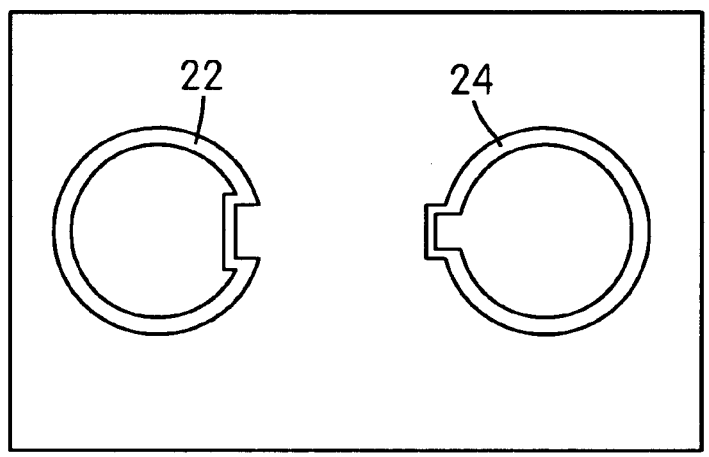
FIG. 10 is a schematic front view of a further embodiment of the connection inlet and outlet.

FIGS. 9 and 10 show two embodiments of the connection inlet 22 and the connection outlet 24. In FIG. 9, the inlet 22 and the outlet 24 are circular but of different diameter. In FIG. 10, the inlet 22 and the outlet 24 have different cross-sectional shapes. In both cases the ends of the duet member and the humidifier inlet and outlet are provided with corresponding engaging formations to avoid incorrect installation. This is especially advantageous when a non-symmetrical or uni-directional humidifier is used.

Although the invention bas been described with reference to a specific examples, it will be appreciated by those skilled in the art, that the invention can be embodied in many other forms.

We claim:

1. An apparatus for supplying breathable gas, the apparatus includes;
    a flow generator;
    a gas outlet;
    a connection means interposed between the flow generator and the gas outlet, the connection means having a connection inlet and a connection outlet; and
    a pressure sensing means interposed between the connection outlet and the gas outlet, wherein the connection means is adapted to allow selective connection to either a duct member providing a direct flow path from the connection inlet to the connection outlet or to a humidifier interposed between the connection inlet and the connection outlet.

2. An apparatus as claimed in claim 1, wherein the breathable gas is air.

3. An apparatus as claimed in claim 1, wherein the apparatus is connected by a gas supply tube to a patient mask to provide Continuous Positive Airway Pressure (CPAP) treatment, assisted respiration or mechanical ventilation.

4. An apparatus as claimed in claim 3, wherein the mask is a nose mask, mouth mask, combination nose and mouth mask, nasal prongs, nasal pillows or full face mask.

5. An apparatus as claimed in claim 1, including a gas flow rate sensing means interposed between the connection outlet and the gas outlet.

6. An apparatus as claimed in claim 5, wherein the gas flow rate sensing means is a pressure differential flow sensor communicating with two pressure ports, the ports being respectively disposed on opposite sides of a flow impedance.

7. An apparatus as claimed in claim 6, wherein one of the ports communicates with the pressure sensing means.

8. An apparatus as claimed in claim 7, wherein the port closest to the gas outlet communicates with the pressure sensing means.

9. An apparatus as claimed in claim 1, wherein the pressure sensing means is an electronic pressure transducer.

10. An apparatus as claimed in claim 1, wherein the connection inlet and the connection outlet are identical.

11. An apparatus as claimed in claim 1, wherein the connection inlet and the connection outlet are different.

12. An apparatus as claimed in claim 11, wherein the connection inlet and the connection outlet are of a different cross-sectional shape or diameter.

13. An apparatus as claimed in claim 1, wherein the connection inlet and the connection outlet are recessed behind the outer edge of the casing or housing of the apparatus.

14. An apparatus as claimed in claim 1, wherein the duct member is in the form of a substantially U-shaped pipe adapted to connect the connecting inlet and the connecting outlet.

15. An apparatus as claimed in claim 14, wherein the U-shaped pipe has an outer panel attached thereto which, upon installation, is substantially flush with adjacent outer panels of the casing or housing.

16. An apparatus as claimed in claim 14, wherein the U-shaped pipe is formed from two joined sections encased in a box having a snap engageable base and lid.

17. An apparatus as claimed in claim 16, wherein the box is snap engageable with a housing or chassis of the apparatus.

18. An apparatus as claimed in claim 1, wherein the humidifier includes a heater.

19. A Continuous Positive Airway Pressure (CPAP) treatment device incorporating the apparatus of claim 1.

20. An apparatus as claimed in claim 1, wherein the connection means is adapted to allow selective manual push-on connection to either the duct member or inlet and outlet tubes of the humidifier.

21. An apparatus as claimed in claim 1, wherein the duct member has a pair of open ends and the humidifier includes an inlet tube with an open inlet end and an outlet tube with an open outlet end, the open end of the duct member being the same size and shape as the open inlet and outlet ends of the inlet and outlet tubes respectively.

* * * * *